(12) United States Patent
Lund et al.

(10) Patent No.: US 11,357,386 B2
(45) Date of Patent: Jun. 14, 2022

(54) ENDOSCOPE ADAPTED FOR FACILITATING BAL PROCEDURES

(71) Applicant: Ambu A/S, Ballerup (DK)

(72) Inventors: Jesper Grøndahl Lund, Ballerup (DK); Morten Jacobsen, Hørsholm (DK); Kaspar Mat Matthison-Hansen, Helsingør (DK); Lasse Markworth Johnsen, Birkerød (DK); Brian Nielsen, Nøstved (DK); Finn Sonnenborg, Frederikssund (DK)

(73) Assignee: AMBU A/S, Ballerup (DK)

( * ) Notice: Subject to any disclaimer, the term of this patent is extended or adjusted under 35 U.S.C. 154(b) by 252 days.

(21) Appl. No.: 16/368,815

(22) Filed: Mar. 28, 2019

(65) Prior Publication Data

US 2019/0223694 A1    Jul. 25, 2019

Related U.S. Application Data

(63) Continuation of application No. PCT/DK2017/050314, filed on Sep. 27, 2017.

(30) Foreign Application Priority Data

Sep. 28, 2016 (DK) .......................... PA 2016 70768

(51) Int. Cl.
*A61B 1/00* (2006.01)
*A61B 1/015* (2006.01)
(Continued)

(52) U.S. Cl.
CPC ...... *A61B 1/00066* (2013.01); *A61B 1/00128* (2013.01); *A61B 1/00147* (2013.01);
(Continued)

(58) Field of Classification Search
CPC ... A61B 1/267; A61B 1/2676; A61B 1/00066; A61B 1/015
See application file for complete search history.

(56) References Cited

U.S. PATENT DOCUMENTS

| 4,222,380 A | 9/1980 | Terayama |
| 4,668,226 A | 5/1987 | Omata et al. |

(Continued)

FOREIGN PATENT DOCUMENTS

| CN | 1466433 A | 1/2004 |
| CN | 101112300 A | 1/2008 |

(Continued)

OTHER PUBLICATIONS

Search Report in corresponding Danish Application No. PA 2016 70768, dated Dec. 23, 2016.
(Continued)

*Primary Examiner* — Alexandra L Newton
*Assistant Examiner* — Rynae E Boler
(74) *Attorney, Agent, or Firm* — Faegre Drinker Biddle & Reath LLP

(57) ABSTRACT

An endoscope having a proximal end and a distal end, a handle at the proximal end and an insertion tube extending from the proximal end towards the distal end. The insertion tube includes an internal working channel extending from the handle to the distal end of the insertion tube. A connector at the handle is adapted for the attachment of a syringe. A recess is adapted to accommodate a cylindrical body of the syringe when said syringe is attached to the connector.

13 Claims, 3 Drawing Sheets

(51) Int. Cl.
*A61B 1/267* (2006.01)
*A61M 1/00* (2006.01)

(52) U.S. Cl.
CPC ............ *A61B 1/015* (2013.01); *A61B 1/2676* (2013.01); *A61M 1/81* (2021.05); *A61B 1/0008* (2013.01)

(56) References Cited

U.S. PATENT DOCUMENTS

| | | | |
|---|---|---|---|
| 4,765,312 | A | 8/1988 | Sasa et al. |
| 5,725,478 | A | 3/1998 | Saad |
| D476,312 | S | 6/2003 | Harris et al. |
| 8,287,500 | B2 * | 10/2012 | Baba ................. A61M 5/31596 604/187 |
| 2002/0082475 | A1 | 6/2002 | Stahl et al. |
| 2006/0229498 | A1 | 10/2006 | Kohno |
| 2007/0049796 | A1 * | 3/2007 | Fujikura ............ A61B 1/00089 600/116 |
| 2008/0027283 | A1 | 1/2008 | Matsui et al. |
| 2008/0033290 | A1 * | 2/2008 | Saadat ............... A61B 1/00096 600/433 |
| 2008/0058650 | A1 | 3/2008 | Saadat et al. |
| 2009/0209478 | A1 | 8/2009 | Nakayama et al. |
| 2009/0209821 | A1 | 8/2009 | Yamane |
| 2009/0306545 | A1 | 12/2009 | Elsakka et al. |
| 2012/0095369 | A1 * | 4/2012 | Teixeira ............. A61B 10/0051 600/582 |
| 2012/0116296 | A1 | 5/2012 | Ducharme et al. |
| 2012/0289858 | A1 | 11/2012 | Ouyang et al. |
| 2014/0360494 | A1 * | 12/2014 | Herskovic ......... A61M 16/0463 128/200.18 |

FOREIGN PATENT DOCUMENTS

| | | |
|---|---|---|
| CN | 101371772 A | 2/2009 |
| CN | 101415362 | 4/2009 |
| CN | 102119039 A | 7/2011 |
| CN | 102149312 A | 8/2011 |
| CN | 105342545 A | 2/2016 |
| CN | 109788886 A | 5/2019 |
| DE | 3725182 C2 | 3/1989 |
| EP | 1 806 090 A1 | 7/2007 |
| EP | 1 882 442 A1 | 1/2008 |
| JP | 2003-310540 A | 11/2003 |
| WO | 2009/152107 A1 | 12/2009 |
| WO | 2010/027109 A1 | 3/2010 |
| WO | WO 2012/060932 A2 | 5/2012 |
| WO | WO 2016/049409 A1 | 3/2016 |
| WO | WO 2016/188542 A1 | 12/2016 |
| WO | WO 2016/188543 A1 | 12/2016 |

OTHER PUBLICATIONS

Search Opinion in corresponding Danish Application No. PA 2016 70768, dated Dec. 23, 2016.
International Search Report and Written Opinion in corresponding International Application No. PCT/DK2017/050314, dated Mar. 23, 2018.
Extended Search Report in related European Application No. 20191676. 4, dated Sep. 30, 2020, 6 pgs.
Intention to Grant under Rule 71(3) EPC related European Application No. 17778182.0 dated Jun. 15, 2020, 6 pgs.
CN Office Action dated Apr. 6, 2021 for CN Application No. 201780056050.
Informal Translation of CN Office Action dated Apr. 6, 2021 for CN Application No. 201780056050.
Office action issued in Chinese Patent Application No. 201780056050. 3, dated Sep. 30, 2021, with informal translation.

* cited by examiner

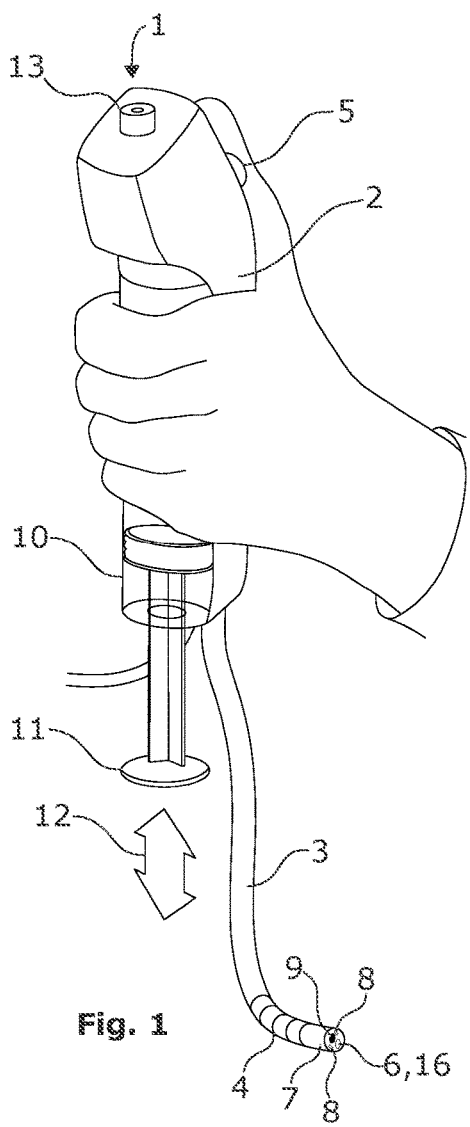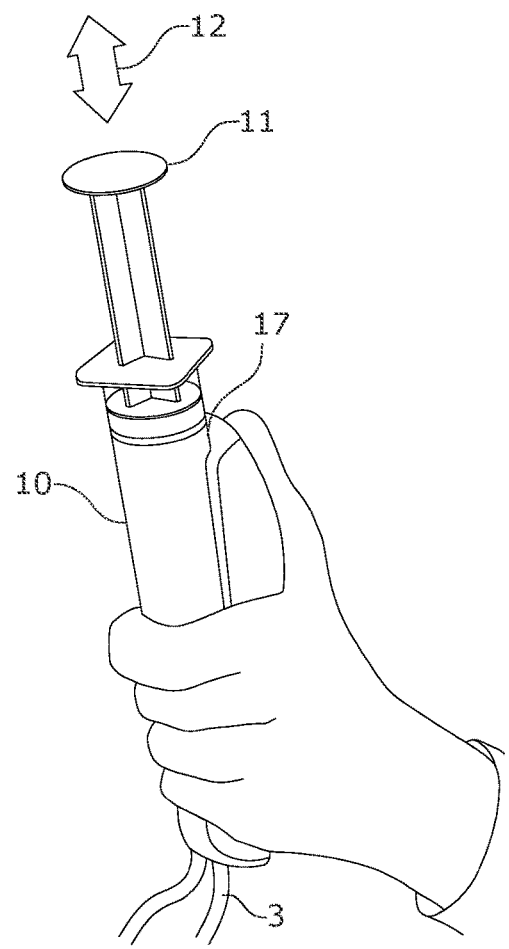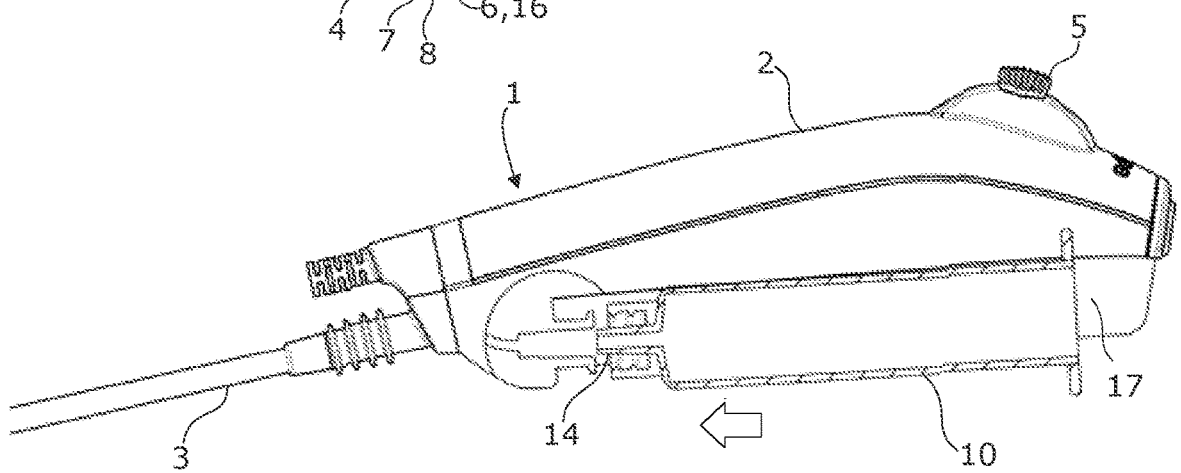

ENDOSCOPE ADAPTED FOR FACILITATING BAL PROCEDURES

CROSS-REFERENCE TO RELATED APPLICATIONS

This application is a continuation of International Application No. PCT/DK2017/050314, filed Sep. 27, 2017, which claims the benefit of Denmark Patent Application No. PA 2016 70768, filed Sep. 28, 2016. The foregoing patent applications are expressly incorporated herein by reference in their entirety.

TECHNICAL FIELD

The present invention relates to an endoscope, more specifically to an endoscope adapted for facilitating BAL procedures.

BACKGROUND

Bronchoalveolar lavage, or BAL, is a commonly used procedure for obtaining samples of organic material from a lung segment of a patient. This is basically done by flushing a lung segment with sterile water and then sucking the water into a sample container. More specifically, the distal end of an endoscope is advanced to the location in the lung where the sample is to be taken. The distal end is then pressed into firm engagement against the interior of the lung to help securing the position in a process commonly referred to as wedging.

Via the working channel of the endoscope, sterile water, e.g. a 0.9% saline solution, is instilled into the lung at the sample location and as much as possible extracted again, now containing organic material, and thus constituting a sample. Typically, this is done by attaching a filled syringe of a volume between 20 ml and 60 ml, e.g. 50 ml to the working channel of the endoscope, via a communication port in the endoscope's handle. The syringe is then used for each insertion as well as the subsequent extraction. This process is normally repeated several times in a row with new syringes, e.g. three to four, the samples being suitable for various purposes, depending which number of sample in the sequence they are, because the composition of the organic material varies. Upon extraction they are therefore normally labelled accordingly. As an alternative to the extraction using the syringe, the extraction may be performed using an external suction and a Lukens trap.

This procedure involves at least two persons (e.g. and operator and an assistant) and quite a lot of preparation. The operator would normally be the doctor in charge of and responsible for the procedure, whereas the assistant would be a nurse. The operator would advance the tip of the endoscope to the desired position, wedge it into position, and decide when to inject the sterile saline solution and when to extract the sample. The assistant would attach and remove the syringes, replace the Luken traps if external suction is used, label the samples, and under some circumstances also operate the syringe and suction at the command of the operator, who decides the correct moment of injection and extraction. To avoid this chain of command it is advantageous when the operator can perform the injections and the extractions. With existing endoscopes, where the syringe is attached to the working channel of the endoscope, e.g. via an intermediate tube, the extraction by the operator by means of the syringe would be extremely difficult, if not impossible, as the operator only has one free hand and would have difficulties retracting the piston of the syringe with that hand only. The other hand of the operator cannot be used, as it is important to maintain the endoscope in the desired position, so as to not move the tip from the wedgedin position.

If external suction is used, the operator would of course be able to activate the suction button on the handle of the endoscope at will, and possibly also depress the piston of the syringe with the other hand. The assistant would still have to replace and label the Lukens trap containing the sample accordingly.

Based on the above it is an object of the present invention to provide an endoscope adapted to facilitate the BAL procedure, including multiple options for work distribution between the operator and the assistant.

SUMMARY

According to a first aspect of the invention this object is achieved by an endoscope comprising a proximal end and a distal end, a handle at the proximal end and an insertion tube extending from the proximal end towards the distal end, the insertion tube comprising a internal working channel extending from the handle to the distal end of the insertion tube, a connector at said handle, said working channel being connected to said connector, and said connector being adapted for the attachment of a syringe, and a recess adapted to accommodate a cylindrical body of the syringe when said syringe is attached to the connector.

This allows the operator to have a firm grip on the syringe with one hand while both injecting the fluid and extracting it again using the other hand. In particular the extraction is advantageous because retracting the piston of a syringe using one hand is in itself awkward, in particular when the syringe has to remain attached to the connector of the port at the endoscope handle. It thus becomes possible for the operator to perform actions which would otherwise have to be performed by the assistant, in turn, giving more flexibility in the work distribution between them.

According to a second aspect this object is achieved by an endoscope comprising a proximal end and a distal end, a handle at the proximal end and an insertion tube extending from the proximal end towards the distal end, the insertion tube comprising a internal working channel extending from the handle to the distal end of the insertion tube, a connector at said handle, said working channel being connected to said connector, and said connector being adapted for the attachment of a syringe, a suction port connectable to an external suction device, and a valve configured to connect the working channel to said external suction device, and a connection means intermediate said suction port and working channel for attaching a fluid trap.

This allows the fluid trap serving as the sample container to be attached directly to the handle of the endoscope where it is readily visible for the operator. The operator therefore has first hand information on the volume, colour, quality etc. of the sample extracted into the sample container, so as to know when to disengage the suction. The sample container moreover may be easily removed because there is only one connection to be severed, i.e. the connection to the handle, rather than the two tubes traditionally connected to a Lukens trap. Since this may also be done by the operator, it becomes possible for the operator to perform actions which would otherwise have to be performed by the assistant, in turn, giving more flexibility in the work distribution between them.

According to a third aspect of the invention the object is achieved by an endoscope having an operating handle comprising a handle housing arranged at a proximal end thereof and an insertion tube extending from said handle towards a distal end of the endoscope and terminating in a tip part at the distal end of the endoscope, the endoscope further comprising a tool arranged at said tip part at the distal end of the endoscope, a tool operating member located at the operating handle, and a control means connecting said tool operating member and said tool, so as to allow linear movement of the tool with respect to the insertion tube in response to activation of said tool operating member, wherein the tool is a suction nozzle adapted to be advanced out of the tip part away from the distal end of the endoscope.

According to a preferred embodiment of the invention, the endoscope further comprises a suction port connectable to an external suction device, and a valve configured to connect the working channel to said external suction device. This allows the operator to have easy and good control over the suction when extracting the liquid sample.

According to a further preferred embodiment, the recess is provided in an outer surface of the handle, in an orientation and location allowing the cylindrical body of a syringe placed in the handle to be gripped during use concurrently with the handle by the same hand of the operator gripping the handle. This provides the operator with a good hold on the syringe, and a good counter force when retraction the piston in order to extract a sample. By gripping the syringe the operator also facilitates tempering of the instillation liquid, which preferably should be at body temperature to decrease patient discomfort. This furthermore increases sample yield because coughing by the patient induced by untempered liquid reduces sample yield.

According to another preferred embodiment, an annular collar has been fitted around the insertion tube at or close to the distal tip. This facilitated the wedging of the tip of the endoscope into the engagement with the lung tissue, and reduces the potential of injury, in particular when the collar is made softer than the distal tip or the insertion tube of the endoscope, e.g. by selection of a soft material.

According to yet another embodiment, the annular collar has a chamfer so as to narrow the circumference of the collar towards the distal end of the insertion tube. This further improves the wedging, and reduces the risk of injury.

According to another preferred embodiment, the connection means comprises means for securing the trap to the handle of the endoscope. Thus only one connection needs to be severed when exchanging the sample container, rather than the two of the traditional Lukens trap.

Preferably, however, the suction port and the connection means are adapted to form a trap at the handle of the endoscope. Thus, still only one connection has to be severed, but the sample container becomes a much simpler construction.

According to a further preferred embodiment, the sampling container comprises an internal precoating, such as a hydrophobic coating, allowing the sample to be readily poured into a storage or shipment container to be sent to the lab.

BRIEF DESCRIPTION OF THE DRAWINGS

The invention will now be described in greater detail based on nonlimiting exemplary embodiments and with reference to the drawings on which, FIG. 1 shows a perspective view of a first embodiment of an endoscope according to the first aspect of the invention, FIG. 2 shows a perspective view of a second embodiment of an endoscope according to the first aspect of the invention, FIG. 3 shows partially crosssectional view of a third embodiment of an endoscope according to the first aspect of the invention.

DETAILED DESCRIPTION

Figure 6:
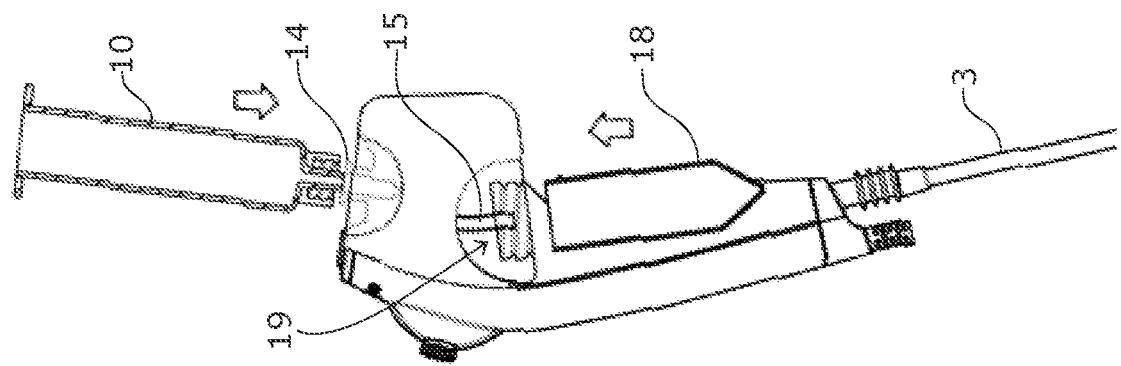
FIG. 6 shows a partially crosssectional view of a third embodiment of an endoscope according to the second aspect of the invention.

Turning first to FIG. 1, an endoscope 1 according to a first embodiment of the invention is shown in normal use where the operator grips the handle 2 with his left hand. The handle 2 forms the proximal end of the endoscope 1. From the handle an insertion tube 3 extends towards the distal end of the endoscope 1 ending in a distal tip 7. An articulated bending section 4 is located at or adjacent the distal tip 7 of the endoscope. The articulated bending section 4 may deflect in response to the operator's thumb moving a control button 5 at the handle. Controlling the deflection of the bending section 4 allows the operator to insert the insertion tube 3 and distal tip 7 of the endoscope into a body cavity of patient, such as into a lung, and maneuver it to a desired location of interest. For this process and for inspection of the location the distal tip 7 of the endoscope 1 is provided with a camera module 9, which allows an operator to visualize the surroundings of the distal tip 7 on a monitor (not shown) connected to the endoscope 1 at the operating handle 2. The distal tip 7 is preferably provided with a first light source 8 such as one or more LEDs to illuminate the surroundings to be visualized by means of the camera module 9.

The endoscope 1 furthermore comprises a working channel 6 ending in a working channel muzzle 16 at the distal tip part 7 and connected to one or more ports 13, 14, 15 located in the handle, and inter alia serving as connectors. In FIG. 1 only one port 13 is visible. These ports 13, 14, 15 may have various purposes, such as inserting specialized tools at the handle 2, and of course instillation and retrieval of liquid. In particular the ports may, as can best be seen in FIGS. 3, 6, and 9, be adapted to fit a Luer Lok® or Luer Taper tip of a syringe and in that sense be a standard connector. The tools may then be guided from the port 13, 14, 15 through the working channel 6 to emerge through the muzzle 16 into the view of the camera module 9, where the operator can view and supervise the use of the tool for its specialized purpose. The working channel 6 may, however, also be used for injection and extraction of fluid, e.g. during the BAL procedure for which the endoscope 1 of the present invention is specially adapted.

One such adaption is that the housing of the handle 2 of the endoscope 1 has a recess 17 adapted to receive a syringe 10 in a position where it may firmly be gripped in a natural manner by the operator when he grips the handle 2 during use of the endoscope. The curvature of the bottom of the recess 17, not visible in FIG. 1, may generally be a circular sector so as to engage the normally cylindrical part of a syringe 10 with a predetermined volume such as 50 ml or 60 ml. Alternatively, the curvature of the bottom may have a shape not matching the cylindrical part of a syringe 10, but being flanked by two upright walls or flanges on which the cylindrical part rests, as indicated in FIG. 3.

Similar to the embodiment of FIG. 3, albeit with an opposite orientation and not visible in FIG. 1, the handle 2 comprises a port 14 located at the end of recess. The location of the port 14 is adapted to the tip of the syringe 10 when located in the recess. That is to say coaxially with the axis of the semi-cylindrical curvature of the recess, or of the cylindrical body of the syringe 10, when the latter is in place in the recess, provided of course the syringe 10 is of a type with a coaxial tip. The latter may not necessarily be the case, as syringes above 5 ml in volume may be designed with concentric or eccentric placement of the nozzle (according to ISO 7886-1). For practical purposes of course a kit with inter alia a disposable endoscope 1 according to the present invention, complete with matching syringes, would be provided. Through this port 14 the sterile saline solution contained in the syringe 10 may be injected into the lung via the working channel 6 by pressing the piston 11 of the syringe 10 in and extracted again by retracting the piston 11 of the syringe 10. Retracting the piston 11 of the syringe 10 will be relatively easy for the operator using his right hand as he has a firm grip on the syringe 10 with his left hand, and thus does not risk detaching the syringe 10 from the port 14, and has a good counterforce so that he does not displace the entire endoscope, and distal tip 7 becomes unstuck from its wedged position in the lung.

To further secure the syringe 10 with respect to the handle 2 the handle may, as also indicated in FIG. 3, be adapted with a suitable thread to receive a Luer Lok® rather than just a Luer Taper. Using a Luer Lok® may, in some circumstances, be inconvenient, and with the good grip on the syringe 10 according to the invention the Luer Taper would suffice.

Figure 8:
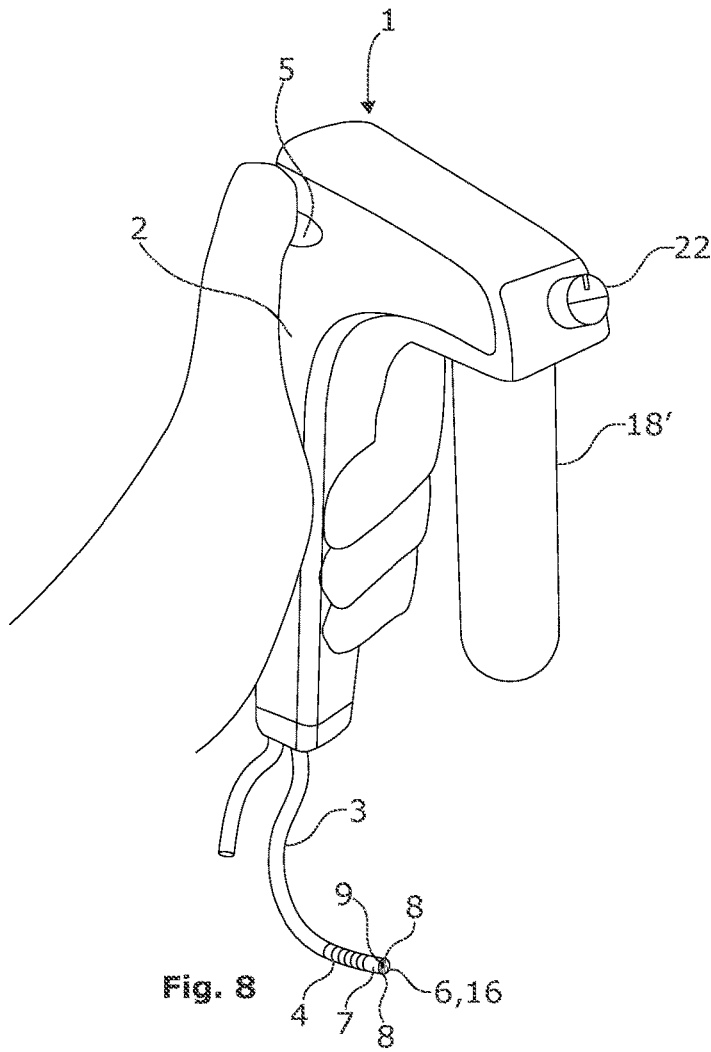
FIG. 8 shows a perspective view of a first embodiment of an endoscope according to the third aspect of the invention.

Also, because circumstances and setup of the BAL procedure varies from location to location, e.g. between hospitals, it is of course not excluded that the extraction of the sample could be performed using the vacuum system normally found in hospitals. Accordingly, the handle 2 of the endoscope 1 of FIG. 1 is also provided with a port 13 to which the vacuum system (wall suction) of the hospital could be attached so as to catch the sample in a Lukens trap (not shown) rather than in the syringe 10. To activate the suction the operator presses a button acting as a suction activator 12. The suction activator is not visible in FIG. 1, but can be seen in the embodiments of FIGS. 4, 5 and 8. The suction activator 12 closes off the inlet of the working channel 6 by means of a valve or the like, and provides a fluid communication from the working channel 6 inside the insertion portion 3 to a sampling container, such as a Lukens trap. Suction is provided by connecting a suction port 13 of the operating handle 2 to a suction device, e.g. a wall outlet. The Lukens trap is then interposed between the handle and the wall outlet, and may be replaced after each sampling.

Preferably, the suction activator gives the operator a greater suction area, so as to make it possible to obtain better and more controlled samples. I.e. the travel length of the suction valve from close to open is long and gives the operator a precise suction.

As indicated above the orientation of the syringe 10 in FIG. 3 is opposite that of FIG. 1. That is to say, the tip of the syringe 10 when placed correctly in the recess generally points towards the proximal end of the endoscope in FIG. 1, whereas in FIG. 3 it generally points towards the distal end of the endoscope. The same applies to the embodiment of FIG. 2. This configuration may be advantageous inasmuch at it matches the direction of insertion and extraction of the fluid. On the other hand, however, this configuration leaves less space for the levers etc. of the control mechanism in the handle 2 for manoeuvring the bending section 4.

Figure 4:
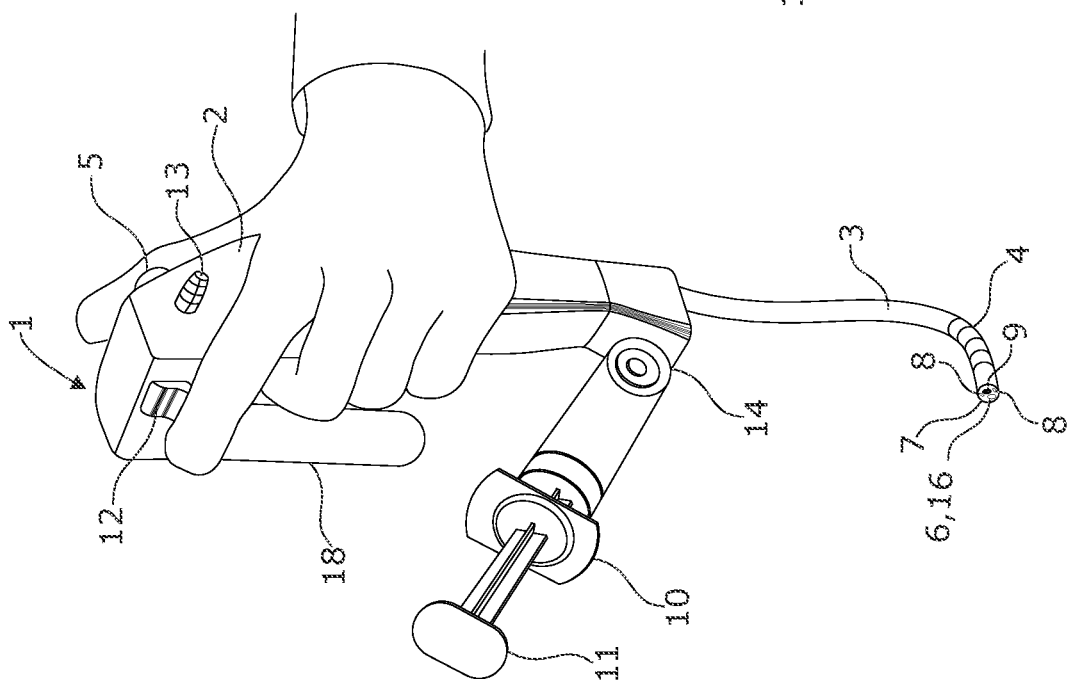
FIG. 4 shows a perspective view of a first embodiment of an endoscope according to the second aspect of the invention.

Turning now to FIG. 4, an endoscope 1 according to a second aspect of the invention is shown. For this embodiment and other embodiments described throughout this application, the same reference numerals as used above in conjunction with the embodiments of FIGS. 1-3 will be used for corresponding features.

Like the endoscope of the first embodiments described above, this endoscope 1 has a handle 2 adapted to be gripped by the left hand of the operator. From the handle 2 forming the proximal end of the endoscope 1, the insertion tube 3 with the bending section 4 extends towards the distal end of the endoscope to terminate in the distal tip 7. In the distal tip 7 a camera module 9, which allows the endoscope to visualize the surroundings of the distal tip 7 on a monitor (not shown) connected to endoscope 1 at the operating handle 2 is located. The distal tip 7 is preferably provided with a first light source 8 such as one or more LEDs to illuminate the surroundings to be visualized by means of the camera module 9. The endoscope 1 furthermore comprises a working channel 6 ending in a working channel muzzle 16 at the distal tip part 7, and connected to one or more ports 13, 14, 15 located in the handle. In FIG. 4 only one port 13 is visible. The port 14 is indicated by a reference numeral, but is not really visible because it is covered by a syringe 10 attached thereto. The port 14 may also be used for other purposes if the endoscope 1 is not used for BAL procedure, such as inserting specialized tools at the handle 2 to be guided from the port 14 through the working channel 6 to emerge through the muzzle 16 into the view of the camera module 9, where the operator can view and supervise the use of the tool for its specialized purpose.

With the attached syringe 10 fluid such as sterile water, e.g. a 0.9% saline solution, may be injected through the working channel 6 and through the muzzle 16, e.g. into the lung for the BAL procedure. The working channel 6 is, however, also be used for injection and extraction of fluid during the BAL procedure for which the endoscope 1 of the present invention is specially adapted. In this embodiment of the endoscope 1, however, extraction using the syringe 10 is not intended, though possible. Accordingly, for the purpose of extraction of the liquid sample using the syringe 10, the port 14 may be provided with a Luer Lok® rather than simply a Luer Taper for firm connection between the syringe 10 and the handle 2. In this respect, it should be noted that since the port 14, and in principle also the ports 13 and 15, may be used for other purposes than injection of fluid, e.g. the abovementioned insertion of tools, it may be suitable to provide adapters for connection between the syringe 10 and or vacuum system such as the wall suction. Such adapters would also be a part of the above-mentioned kit for the BAL procedure.

Rather than extracting the fluid sample from the lung using the syringe 10, the endoscope of FIG. 4 is provided with a fitting for a sample container 18, e.g. a thread as shown in the similar embodiment of FIG. 6. As can be seen, the handle has a protrusion towards the right-hand side as seen from the user perspective in FIG. 4. In this respect it should be noted that references to left, right, up, down etc. regarding the handle or other parts of the endoscope, are to be seen from the operator's view holding the endoscope 1 in front of himself in his left hand with the insertion tube 3 generally being straight and pointing downward. Though the bending section 4 may be deflected before insertion into a patient, e.g. for testing, the skilled person will understand that the insertion tube 3 is generally straight, and does not yet have curvatures as the ones shown in FIGS. 1, 2, 4 and 8.

Suction is applied to a chamber 19 in the handle 2 or directly into the sample container 18 via a separate tube (not show) so as to extract fluid via the working channel 6. The suction is provided by an external vacuum system such as wall suction via a hose attached to the port 13 in a manner known per se. The suction to the working channel 6 may then be activated by a suction activator 12, such as a button. The suction activator 12 communicates with a valve or otherwise closes off the inlet of the working channel 6 and provides a fluid communication from the working channel 6 inside the insertion tube 3 to a sample container 18, via a outlet tube 15 located in the sample container 18, when the latter is in its attached position on the handle 2. The sample container 18 together with the outlet tube 15 thus forms a trap for the liquid sample. Alternatively, a separate trap could be fitted.

The fitting for the sample container 18 is located below the protrusion so as to allow the liquid of the sample to fall down into the sample container 18 under the influence of gravitation when it leaves the outlet tube 15.

Figure 5:
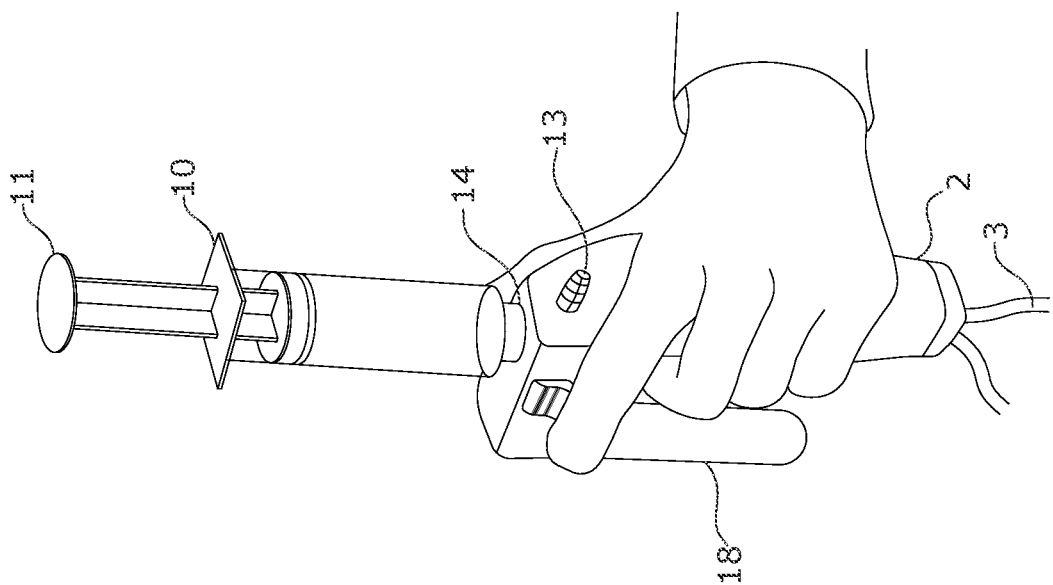
FIG. 5 shows a perspective view of a second embodiment of an endoscope according to the second aspect of the invention.

Turning now to FIG. 5 a further embodiment of the endoscope 1 according to the invention is show. Essentially the endoscope 1 differs only from the in the location of the port 14 to which the syringe 10 is to be attached. Evidently, however, this necessitates a different design of the working channel 6, the suction activator, valves etc. within the handle 2, but this is largely a matter of choice and as such of little relevance to the invention. The main difference between the embodiments of FIG. 4 and FIG. 5 is thus the orientation of the attached syringe, where the orientation shown in FIG. 4 may be more suitable for activation by an assistant, whereas the orientation shown in FIG. 5 may be more suitable for operation by the operator himself. In both cases, however, the operator may himself be in control of the suction. Also, the sample container is readily accessible by both the assistant and by the right hand of the operator himself, thus leaving more options in the work distribution between the operator and the assistant. Furthermore, with the position of the sample container 18 below the protrusion, it becomes relatively easy for both the assistant and the operator to visually inspect it, e.g. in order to see if it is full or when all fluid has been extracted from the lung and no more is exiting the outlet tube 15. Also, during suction the sampling volume, colour, quality etc. is easy to see for the operator.

FIG. 6 as indicated above shows an embodiment similar to those of FIGS. 4 and 5. It is adapted for attaching the syringe 10 to a port 14 arranged at the proximal end of the handle 2 of the endoscope 1. However, instead of the lateral attachment of the sample container 18, the sample container 18 is arranged in a position where it can, similar to the arrangement of FIGS. 1-3, be gripped firmly by the hand of the operator.

Figure 7:
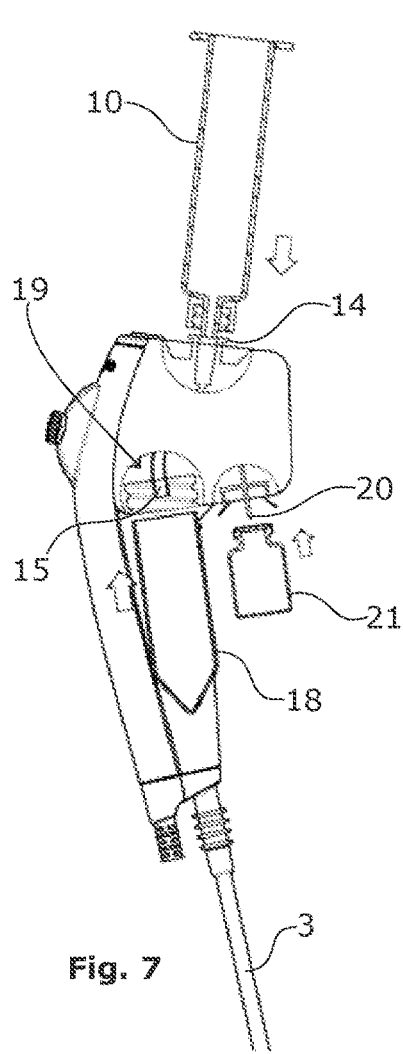
FIG. 7 shows a partially crosssectional view of a fourth embodiment of an endoscope according to the second aspect of the invention.

FIG. 7 shows an arrangement similar to that of FIG. 6 differing essentially only in that a receptacle 20 for attaching a vial 21 is provided. From this vial 21, further liquid may be introduced into the working channel 6, in particular a local anaesthetic such as Lidocaine, e.g. to prevent coughing reactions when inserting the insertion tube 3. Though not shown, the skilled person would understand that the position of the port 14 for attaching the syringe 10 and the position of the receptacle 20 for attaching the vial 21 could be swapped, so as to allow gravitation to assist the introduction of the further fluid into the working channel 6.

FIG. 8 again shows an endoscope 1 with a handle 2 more similar to that of FIG. 5. However, instead of using both a syringe 10 and a sample container 18 the handle is adapted to cooperate with a sample container 18' that doubles both as a reservoir for the fluid to be injected, and for the extracted sample. Thus, the handle 2 is fitted with a turn knob connected to a valve or the like for switching the direction of the suction as applied from the external vacuum source, and attached to the port 13 and activated by the suction activator 12. Both the port 13 and the suction activator 12 are located in the same places on the handle 2 as shown in FIG. 5 and are thus not visible in FIG. 8. Thus by turning the knob 22 between two different positions and the activating the external suction fluid may either be extracted from the sample container and injected into the lung, or extracted from to lung into the sample container 18' again.

Figure 9:
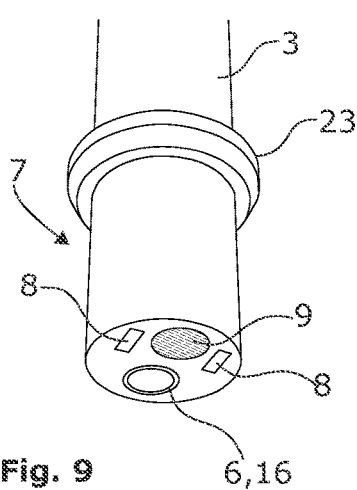
FIG. 9 shows a perspective view of details of the distal tip of an endoscope according to the present invention.

Turning now to FIG. 9 details of the distal tip 7 of the endoscope 1 optionally incorporable in any of the previously described embodiments. As can be seen the distal tip 7 comprises the suction muzzle 16 at the end of the working channel 6. Next to the muzzle 16 the illumination LED 8 and the camera module 9, as described above, are located. For adapting the endoscope 1 to the use for the BAL procedure, an annular collar 23 has been fitted around the insertion tube 3 at or close to the distal tip 7. The annular collar 23 is made of a material which is softer than the materials of which the distal tip 7 and of the insertion tube 3 are made, as well as softer i.e. easier deformable than the distal tip 7 and the insertion tube 3 as such. This facilitates the wedging of the distal tip 7 in the desired lung segment during the BAL procedure and secures the position better. Being softer it also carries a lower potential for damage to the lung tissue, during the wedging. To further facilitate the wedging, the annular collar 23 furthermore has a chamfer 24 so as to narrow the circumference of the collar towards the distal end of the insertion tube 3. As an alternative to making the annular collar 23 of a soft material and with a taper would be to provide an inflatable collar at or close to the distal tip 7. The wedging and securing in place would then be performed by inflating the inflatable cuff once it is in the correct location, the inflated collar would then be cushioned by the air inside, so as to softly engage the surrounding tissue in the desired lung segment.

Figure 10:
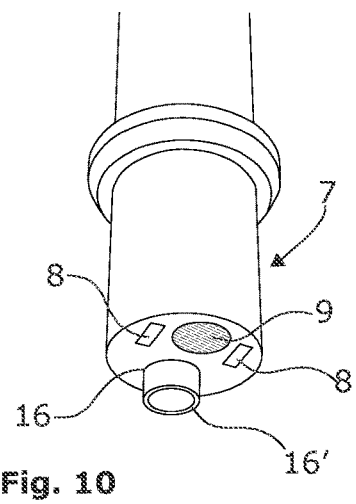
FIG. 10 shows a perspective view of a suction nozzle advanced in front of the distal tip of the endoscope according to the present invention.

In FIG. 10 further details of the distal tip 7 of the endoscope 1 optionally incorporable in any of the previously described embodiments are shown. Accordingly, the distal tip 7 comprises the previously described illumination LED 8 and the camera module 9. However, as mentioned above the working channel 6 can be used for advancing tools as well. Such tools may be integrated in the endoscope 1 or they may be advanced from an entry port at the handle 2, e.g. the entry port 13 of FIG. 1. If the tool is integrated in the endoscope 1, the tool may be operated by means of a tool operating member located in a suitable manner at the operating handle 2 so as to be operable by the operator. Such tool operating arrangements are per se well known, e.g. from WO2016/188542 or WO2016/188543 both of which are incorporated herein by reference, and thus not illustrated. In the illustrated embodiment the tool comprises a suction nozzle 16'. The suction nozzle 16' may be advanced out of the muzzle 16 to a position, as shown, in front of the distal tip 7 of the endoscope 1. This has two advantages. First is that the nozzle 16' is moved away from the camera module 9, so that when the suction creates turbulence in the liquid to be extracted, the vision of the camera module 9 and hence the operator is not blurred by the turbulence. The operator thus will have a better view to what he is doing. By having a better view of what is going on, the operator is able to moderate the suction as to avoid collapse of the lung segment. Collapsing the lung segment prevents extraction, and further increases patient recovery time. The other is that the diameter of the suction nozzle 16' is much smaller than that of the distal tip part 7. Accordingly, the suction nozzle 16' may be advanced to places narrower than those accessible with the distal tip part 7 itself, and samples may thus be taken from places not that cannot be reached by the muzzle 16.

According to a further preferred embodiment, the sampling container 18 comprises an internal precoating, such as a hydrophobic coating, or other coating allowing the sample to be readily poured into a storage or shipment container to be sent to the lab. E.g. the sample container may be pre-siliconized to minimize cell adherence to the surface. This would allow these shipments containers to be suitably labelled in advance, in turn allowing more flexibility in the actual BAL procedure, because the assistant would have one less thing to take care of. With a suitably hydrophobic coating the sampling container may even be reused 18 for the next sample in the sequence. Any contaminants from the previous sample would be negligible, given that the sample are already taken from the same place in the same patient in a short continuous sequence. The pre-coated sample container, may be a fluid trap, or any other suitable container including in principle a syringe as described above.

What is claimed is:

1. An endoscope comprising:
    a proximal end and a distal end;
    a handle at the proximal end, the handle comprising a middle section and a proximal end opposite a distal end, the middle section extending between the proximal end and the distal end of the handle, the middle section comprising an external surface including a first surface opposite a recess surface defining a recess;
    an insertion tube extending from the distal end of the handle towards the distal end of the endoscope, the insertion tube comprising a working channel extending internally from the handle to the distal end of the insertion tube; and
    a connector at said handle connected to said working channel and adapted to attach a syringe;
    wherein the recess is sized and shaped to accommodate a cylindrical body of the syringe when said syringe is attached to the connector, the cylindrical body of the syringe having a near side located, in use, facing the recess surface and a far side opposite the near side, the recess surface having an elongate concave arcuate shape configured to receive the near side of the cylindrical body of the syringe;
    wherein the handle is devoid of structure extending along the middle section opposite the recess surface and the first surface; and
    wherein the recess is provided in an orientation and location allowing the operator to simultaneously grip with one hand the handle and the cylindrical body of the syringe, placed in the recess, with the palm of the hand resting on the first surface and at least one finger wrapping around, and resting on, the far side of the cylinder directly opposite the recess surface.

2. The endoscope of claim 1, further comprising a suction port connectable to an external suction device, and a valve configured to connect the working channel to said external suction device.

3. The endoscope of claim 1, further comprising a distal tip at the distal end and an annular collar fitted around the insertion tube at or close to the distal tip.

4. The endoscope of claim 3, wherein the annular collar has a chamfer narrowing a circumference of the collar in a direction towards the distal end of the insertion tube.

5. The endoscope of claim 2, further comprising a distal tip at the distal end and an annular collar fitted around the insertion tube at or close to the distal tip.

6. The endoscope of claim 5, wherein the annular collar has a chamfer so as to narrow the circumference of the collar towards the distal end of the insertion tube.

7. The endoscope of claim 2, wherein the connector is positioned at the proximal end of the handle facing toward the distal end of the handle.

8. The endoscope of claim 7, wherein the suction port is positioned at the proximal end of the handle facing away from the distal end of the handle.

9. The endoscope of claim 2, wherein the connector is positioned at the distal end of the handle facing towards the proximal end of the handle.

10. The endoscope of claim 2, wherein the connector is positioned intermediate the suction port and the working channel.

11. The endoscope of claim 10, wherein the suction port and the connector are adapted to form a fluid trap at the handle of the endoscope.

12. The endoscope of claim 11, wherein the fluid trap comprises an internal coating.

13. The endoscope of claim 1, wherein the handle is devoid of structure extending along the middle section opposite the recess that could, in use, prevent the at least one of the ring, middle and index finger sized and shaped such that in use the thenar eminence of the palm of same hand of the operator rests on the first surface and at least one of the ring, middle and index fingers can press the cylindrical body of the syringe toward the recess surface.

* * * * *